(12) United States Patent
Schill

(10) Patent No.: US 10,638,733 B2
(45) Date of Patent: *May 5, 2020

(54) DEVELOPMENT OF YY MALE FISH BROODSTOCKS IN A SINGLE GENERATION

(71) Applicant: Daniel J. Schill, Boise, ID (US)

(72) Inventor: Daniel J. Schill, Boise, ID (US)

(73) Assignee: Fisheries Management Solutions, Inc., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/536,022

(22) Filed: Aug. 8, 2019

(65) Prior Publication Data

US 2019/0364858 A1   Dec. 5, 2019

Related U.S. Application Data

(63) Continuation of application No. PCT/US2018/017705, filed on Feb. 9, 2018.

(60) Provisional application No. 62/483,747, filed on Apr. 10, 2017, provisional application No. 62/457,033, filed on Feb. 9, 2017.

(51) Int. Cl.
| | |
|---|---|
| *A01K 67/027* | (2006.01) |
| *A01K 67/02* | (2006.01) |
| *A01K 61/10* | (2017.01) |
| *A01K 67/033* | (2006.01) |
| *C12N 15/85* | (2006.01) |

(52) U.S. Cl.
CPC .............. *A01K 67/02* (2013.01); *A01K 61/10* (2017.01); *A01K 67/027* (2013.01); *A01K 67/0338* (2013.01); *C12N 15/85* (2013.01); *A01K 2207/10* (2013.01); *A01K 2227/40* (2013.01); *A01K 2227/50* (2013.01); *A01K 2227/70* (2013.01); *C12N 2015/8527* (2013.01)

(58) Field of Classification Search
CPC .................................................... A01K 67/02
USPC ......................................................... 800/20
See application file for complete search history.

(56) References Cited

U.S. PATENT DOCUMENTS

2004/0073959 A1   4/2004   Thresher et al.

FOREIGN PATENT DOCUMENTS

| BR | PI100389507 A2 | 3/2013 |
|---|---|---|
| CN | 103798169 A | 5/2014 |
| CN | 107079844 A | 8/2017 |

OTHER PUBLICATIONS

Andrew, M. N., O'Conner, W. A., Dunstan, R. H., and G. R. MacFarlane, 2010. Exposure to 17 alpha ethynylestradiol causes dose and temporally dependent changes intersex, females and vitellogenin production in the Sydney rock oyster. Ecotoxicology 19: 1440-1451.

Bongers, A. B. J., B. Zandieh-Doulabi, C. J. J. Richter, and J. Komen 1999. Viable Androgenetic YY Genotypes of Common Carp *Cyprinus carpio* L. Journal of Heredity 90(1): 195-198.

Cotton, S., and C. Wedekind, 2007. Control of introduced species using Trojan sex chromosomes. Trends in Ecology and Evolution 22:441-443.

Gagne, F., Blaise, C., Pellerin, J., Pelletier, E., Douville, M., Gauthier-Clerc, S., and L Viglino, 2003. Sex alteration in soft-shell clams in an intertidal zone of the Saint Lawrence River, Quebec, Canada. Comparative Biochemistry and Physiology Part C 134: 189-198.

Gutierrez, J. B., and J. L. Teem, 2006. A model describing the effect of sex-reversed YY fish in an established wild population: the use of a Trojan Y chromosome to cause extinction of an introduced exotic species. Journal of Theoretical Biology 241:333-341.

Jiang, M., X. Wu, K. Chen, H. Luo, W. Yu, S. Jia, Y. Li, Y. Wang, P. Yang, Z. Zhu and W. Hu, 2018. Production of YY Supermale and XY Physiological Female Common Carp for Potential Eradication of this Invasive Species. Journal of The World Aquaculture Society 10.1111/jwas.12492.

Kennedy, P., K. A. Meyer, D. J. Schill, M. R. Campbell, N. Vu, and N.V. Vu. in press. Survival and reproductive success of hatchery YY male Brook Trout stocked in Idaho Streams. Transactions of the American Fisheries Society.

Kogan, M., 1998. Integrated pest management: Historical perspectives and contemporary developments. Annual Review of Entomology 43:243-70.

Liu, H., R. Guan, J. Xu, C. Hou, H. Tian, and H. Chen, 2013. Genetic manipulation of sex ratio for the large-scale breeding of YY super-male and XY all-male Yellow Catfish (Pelteobagrus fulvidraco (Richardson)). Marine Biotechnology 15:321-328).

Mair, G. C., J. S. Abucay, D. O. F. Skibinski, T. A. Abella, and J. A. Beardmore, 1997. Genetic manipulation of sex ratio for the large-scale production of all-male tilapia Oreochromis niloticus. Canadian Journal of Fisheries and Aquatic Sciences, 54:396-404.

Makhrov, A. A., D. P. Karabanov, and Y. V. Koduhova, 2014. Genetic methods for the control of alien species. Russian Journal of Biological Invasions 5:194-202.

Muir, W. M., and R. D. Howard, 2004. Characterization of environmental risk of genetically engineered (GE) organisms and their potential to control exotic invasive species. Aquatic Sciences 66:414-420.

(Continued)

*Primary Examiner* — Valarie E Bertoglio

(74) *Attorney, Agent, or Firm* — Zeman-Mullen & Ford, LLP

(57) ABSTRACT

This disclosure describes exemplary embodiments of a method of creating a YY animal broodstock, preferably in a single generation, wherein the broodstock includes only sperm-producing YY males and egg-producing YY males, the method comprising the steps of: (a) creating YY males via androgenesis; (b) exposing selected ones of the YY males created in step (a) to a feminizing hormone; and (c) identifying sperm-producing YY males and egg-producing YY males from among the YY males created in steps (a) and (b). In other embodiments, the method further comprises: (d) repeating steps (a) through (c) N times in order to produce N unrelated families of sperm-producing YY males and egg-producing YY males; and (e) cross-breeding various ones of the unrelated families produced in step (d) in order to produce a genetically-diverse YY progeny. In some embodiments, N may be about 60.

20 Claims, 5 Drawing Sheets

(56) References Cited

OTHER PUBLICATIONS

Parshad, R. D., 2011. Long time behavior of a PDE model for invasive species control. International Journal of Mathematical Analysis 5:1991-2015.

Piferrer, F. 2001. Endocrine sex control strategies for the feminization of teleost fish. Aquaculture 197:229-281.

Schill D. J., J. A. Heindel, M. R. Campbell, K. A. Meyer, and E. R. J. M. Mamer, 2016. Production of a YY Male Brook Trout broodstock for potential eradication of undesired Brook Trout populations. North American Journal of Aquaculture 78:72-83.

Schill, D. J., K. A. Meyer, and M. J. Hansen, 2017 Simulated effects of YY Male stocking and manual suppression for eradicating non-native Brook Trout populations. North American Journal of Fisheries Management 37:5, 1054-1066.

Shelton, W. L. and S. D. Mims, 2003. Fabrication of Silastic Implants for in Vivo Steroid Delivery in Fish, North American Journal of Aquaculture, 65:2, 158-161.

Teem, J. L., and J. B. Gutierrez, 2010. A theoretical strategy for eradication of Asian Carps using a Trojan Y Chromosome to shift the sex ratio of the population. American Fisheries Society Symposium 74:1-12.

Thresher, R. E, K. Hayes, N. J. Bax, J. Teem, T. J. Benfey, and F. Gould, 2014. Genetic control of invasive fish: technological options and its role in integrated pest management. Biological Invasions 16:1201-1216.

Tsehaye, I, Catalano, M., Sass, G. Glover, D. and B Roth, 2013. Prospects for fishery-induced collapse of invasive Asian Carp in the Illinois River. Fisheries 38: 445-454.

Zhang, D. 2016. Transgenic Disruption of Aromatase Using the Daughterless Construct to Alter Sex Ratio in Common Carp, Cyprinus Carpio. M.S. Thesis, Auburn University.

Senior, A. M., P. M. Lokman, G. P. Gloss, and S. Nakagawa, 2015. Ecological and evolutionary applications for environmental sex reversal of fish. The Quarterly Review of Biology 90:23-44.

Komen, H. and G. H. Thorgaard 2007. Androgenesis, gynogenesis and the production of clones in fishes: a review. Aquaculture 269:150-170.

Sarder, M. R. I., Penman, D. J., Myers, J. M. and McAndrew, B.J. 1999. Production and Propagation of Fully Inbred Clonal Lines in the Nile Tilapia (*Orechromis niloticus* L.). Journal of Experimental Zoology 284:675-685.

Tave, Douglas. Inbreeding and brood stock management. FAO Fisheries Technical Paper 392.

International Search Report and The Written Opinion of the International Searching Authority in related PCT application No. PCT/US2018/017705 dated Apr. 9, 2018 (8 pages).

Certified Translation of Brazilian Patent Application No. PI 100389507 published Mar. 19, 2013.

DEVELOPMENT OF YY MALE FISH BROODSTOCKS IN A SINGLE GENERATION

RELATED APPLICATIONS AND PRIORITY CLAIM

This application is a continuation application claiming benefit under 35 U.S.C. § 365, and priority to, and commonly-invented International Application No. PCT/US2018/017705 filed Feb. 9, 2018, which designates the U.S., and which further claims the benefit of, and priority to, the following two commonly-invented U.S. Provisional Patent Applications: (1) Ser. No. 62/457,033, filed Feb. 9, 2017; and (2) Ser. No. 62/483,747, filed Apr. 10, 2017. The entire disclosures of PCT/US2018/017705, 62/457,033 and 62/483,747 are further incorporated herein by reference.

FIELD OF THE DISCLOSURE

This disclosure is directed generally to eradicating invasive fish species, and more particularly to eradication via development of YY male fish broodstocks, preferably in a single generation, for use in a Trojan Y chromosome program.

BACKGROUND OF THE DISCLOSED TECHNOLOGY

Worldwide, invasive fish cause tens of millions of dollars (US$) in ecosystem and fisheries damage annually and are increasingly targeted for chemical or manual removal in streams and lakes. However, piscicides are non-selective and socially/environmentally unacceptable in some locales, while complete population eradication via conventional manual removal methods like netting or electrofishing is unpredictable and often ineffective as a few invasive individuals often survive to re-build large populations (Makhrov et al. 2014). A new method, the YY male or Trojan Y Chromosome (TYC) approach, relies on development of a hatchery broodstock whose progeny (when stocked) incorporate a second Y chromosome into the undesired wild population. Theoretically, if enough YY males are stocked into the target population over time, the population will skew toward all males, eradicating the undesired population upon stocking cessation (Gutierrez and Teem 2006; Them and Gutierrez 2010). Based on the optimistic predictions in the above two theoretical modeling studies, Schill et al. (2016) developed a YY male broodstock for Brook Trout, the first such broodstock specifically developed for field use in eradicating invasive populations. Subsequent pilot field studies indicate that stocked YY males effectively reproduce with wild females and the results are considered proof-of-concept for the TYC approach in Brook Trout (Kennedy et al., in press).

Despite the success in the TYC approach to date, there is a long felt but unsolved need in the art, in that current techniques require at least three generations to develop YY male broodstocks (see Detailed Description below). Even in the case of rapid-maturing species like the Brook Trout, conventional methodologies require 5 years to create suitable numbers for small pilot field trials and 6-7 years for largescale YY male production capability. In later maturing invasive species like Asian carp currently invading the Mississippi River basin (United States) with catastrophic results (see, e.g. Tsehay et al. 2013), it could take 20+ years to create a YY male broodstock using the same conventional approach as that used for Brook Trout. Such long and costly broodstock development times for late-maturing species are unlikely to interest natural resource managers tasked with halting immediate ecosystem damage. The art needs a technique that develops YY male broodstocks in less than three generations, and preferably in a single generation.

Technology described in this disclosure solves the need by providing a TYC broodstock that may preferably be produced in a single generation, thereby substantially reducing the time required to create suitable numbers of YY males to launch an effective interdiction. Although many of the techniques combined to produce this result have existed by themselves for some time, the combination of the techniques as described herein is new, and yields surprising and unexpected results, in that the combination is substantially greater than "the sum of the parts". The first step in the disclosed process is to use androgenesis to produce YY male fish (rather than the usual XY arrangement). Androgenesis is not new and has been used in limited commercial aquaculture settings and to produce clones for research purposes (Koman and Thorgaard 2007). Likewise, step two in the disclosed process (feminization of YY male fish using estrogenic hormones) has existed for decades for a variety of species (Piferrer 2001). The third step of the disclosed process (identification of an individual fish's sex using genetic methods) is a more recent scientific development but has also been used for a variety of purposes including the development of YY male fish using the much slower three generation approach (Schill et al. 2016). No known prior work has combined the use of these three procedures to produce a YY male broodstock, preferably in a single generation, that may then be genetically diversified with two standard broodstock production techniques in order to be ready for release into the wild.

Indeed, and in sharp contrast, traditional thinking would more likely have suggested gene modification as the technology from which YY male broodstocks could be developed in a single generation. For example, the "daughterless" approach purports to create a genetically modified organism (GMO) via gene splicing whose progeny are genetically programmed to only produce male offspring (Thresher et al. 2004). Although both the daughterless method and the disclosed inventive YY male approach outlined below in the Detailed Description both seek to drive the sex ratio of wild populations to all male, thereby eradicating the undesired population, the two approaches utilize vastly different methodologies. Further, recent study of the "daughterless" approach described initially by Thresher et al. indicates it that, at least as applied to common carp, the methodology still produces "daughters" (Zhang 2016). The methodology is thus suspect and may even be inoperable in addressing species eradication in the field.

Other reported recent work is also worthy of note as background. Jiang et al, appear to have been working contemporaneously and independently in China on similar subject matter to the technology described herein (Jiang et al. 2018). Jiang et al.'s work focuses on androgenesis and to a lesser extent, sex reversal. They report that they considered the Trojan Y chromosome strategy to be one of the most promising methods to eradicate invasive species, but that, in their view, obtaining fertile YY supermales (MYY) and YY physiological female (phenotypic) females (FYY) is a very difficult process. The production of viable sperm-producing MYY common carp is not new (e.g. Bongers et al. 1999, Koman and Thorgaard 2007). However, Jiang et al.'s androgenetic work produced viable androgenetic MYY broodstock, which were then identified by paternity testing and test crossing. Using estrogen exposure to induce sex reversal, Jiang et al. report that they were able to produce feminized males or FXY carp (a result that has also been reported in earlier journals). Some of the Jiang et al. authors appear as inventors on China patent application CN 20171315756, effective filing date May 8, 2017.

Importantly, neither the referenced publication by Jiang et al., nor the referenced China patent application are prior art to this disclosure. However, the apparent contemporaneous independent work by Jiang et al. suggests strongly that the methodologies generally disclosed herein address a long felt and unsolved need (eradication of invasive species) with a nonobvious approach.

References cited in and/or relevant to this Background section:

Bowers, A. B. J., B. Zandieh-Doulabi, C. J. J. Richter, and J. Komen 1999. Viable Androgenetic YY Genotypes of Common Carp *Cyprinus carpio* L. Journal of Heredity 90(1): 195-198.

Gutierrez, J. B., and J. L. Teem. 2006. A model describing the effect of sex-reversed YY fish in an established wild population: the use of a Trojan Y chromosome to cause extinction of an introduced exotic species. Journal of Theoretical Biology 241:333-341.

Xiang M., X. Wu, K. Chen, H. Luo, W. Yu, S. Jia, Y. Li, Y. Wang. P. Yang, Z. Zhu and W. Hu. 2018. Production of YY Supermale and XY Physiological Female Common Carp for Potential Eradication of this Invasive Species. Journal of The World Aquaculture Society 10.1111/jwas.12492. See also China patent application CN 20171315756, effective filing date May 8, 2017.

Kennedy, P., K. A. Meyer, D. J. Schill, M. R. Campbell, N. Vu, and N. V. Vu. in press. Survival and reproductive success of hatchery YY male Brook Trout stocked in Idaho Streams. Transactions of the American Fisheries Society.

Koman, H. and G. H. Thorgaard 2007. Androgenesis, gynogenesis and the production of clones in fishes: a review. Aquaculture 269:150-170.

Makhrov, A. A., D. P. Karabanov, and Y. V. Koduhova, 2014. Genetic methods for the control of alien species. Russian Journal of Biological Invasions 5:194-202.

Piferrer, F. 2001. Endocrine sex control strategies for the feminization of teleost fish. Aquaculture 197:229-281.

Schill D. J, J. A. Heindel, M. R. Campbell, K. A. Meyer, and E. R. J. M. Mamer, 2016. Production of a. YY Male Brook Trout broodstock for potential eradication of undesired Brook Trout populations, North American Journal of Aquaculture 78:72-83.

Them, L., and J. B. Gutierrez, 2010. A theoretical strategy for eradication of Asian Carps using a Trojan Y Chromosome to shift the sex ratio of the population. American Fisheries Society Symposium 74:1-12.

Thresher, R, Groyne, P., Patil, J. and L. Hinds, 2004. Genetic control of sex ratio in animal populations. United States Patent Application Publication 2004/0073959 A1.

Tsehay, I, Catalano, M., Sass, G. Glover, D. and B Roth, 2013. Prospects for fishery-induced collapse of invasive Asian Carp in the Illinois River. Fisheries 38: 44-454.

Zhang. D. 2016. Transgenic Disruption of Aromatase Using the Daughterless Construct to Alter Sex Ratio in Common Carp, *Cyprinus Carpio*. M. S. Thesis, Auburn University.

SUMMARY AND TECHNICAL ADVANTAGES

As noted, the problems of the prior art are addressed in this disclosure by a method for developing YY male fish broodstocks, preferably in a single generation, for use in a Trojan Y Chromosome program directed to eradicating invasive fish species. The goal of the inventive procedure described in the Detailed Description section below is to rapidly produce a hatchery broodstock of genetically YY male fish via the combined use of three hitherto unrelated scientific procedures not known or suggested to be used in combination previously. Once this broodstock is produced via the disclosed procedure and spawned, large numbers of the resulting progeny become available for release into a given wild population. Continued stocking of hatchery-produced YY males according to this disclosure will eventually create an all-male (XY) population in the wild, starving the wild population of its ability to produce eggs for natural progeny. The overall result is complete eradication of the undesired species in a given water body or stream.

The combined use of three separate scientific procedures will result in a YY male hatchery broodstock in a single generation, an important aquaculture advance with immediate implications for the control and/or eradication of a wide variety of invasive fish. Once this broodstock, comprised of both sperm- and egg-producing individuals, is matured and spawned in the hatchery, large numbers of the progeny (all sperm-producing YY males) may subsequently be produced for release into wild populations.

Although simulations suggest the stocking of YY males may very well prove useful in eliminating well established invasive populations, the release of YY males at, or immediately above, the point of invasion of an exotic species may halt the upstream advance into new waters and may be the most efficacious use of the TYC technique.

The use of TYC or YY male concept for eliminating invasive fish may also be expandable to explosively invasive Dreissenid mussels or other exotic shellfish and potentially invasive reptiles and amphibians if the eggs of specific species of interest prove responsive to estrogenic hormones.

It is therefore a primary technical advantage of the disclosed YY male broodstock development method to produce the broodstock, preferably in a single generation. This is an important aquaculture advance. Prior efforts to produce YY male broodstocks have required cultivation times ranging from 3 generations (Schill et al. 2016) to up to 5 generations that include time-consuming progeny testing (Liu et al. 2013; Mair et al. 1997). In contrast, the new disclosed approach can create a hatchery YY male broodstock for a given species in one generation, drastically reducing production costs and years required for implementation of a TYC eradication effort. Indeed, without limitation, the preferred one-generation approach described in this disclosure has utility and industrial applicability to making the so-called Trojan Y Chromosome method (Gutierrez and Teem 2006), also known as the YY male approach (Schill et al. 2016), available to control and eradicate some of the most highly destructive invasive fish in the U.S. (e.g. Common Carp) and, in particular, late-maturing species (e.g. 3 Asian carp species and Lake Trout).

A further technical advantage of the disclosed YY male broodstock development method is that it is a highly advantageous substitute for the so-called "daughterless" method currently under laboratory evaluation for species eradication in some applications (Thresher et al. 2004). The daughterless method relies on the creation of a transgenic construct via gene splicing, while the disclosed YY male approach does not. In short, the daughterless method involves the creation and irreversible release of a genetically modified organism (GMO) into the wild, a subject of much ethical and environmental controversy (e.g., Muir and Howard 2004). In contrast, the YY male approach is reversible (Cotton and Wedekind 2007) and not a GMO (Senior et al. 2015) and thus comprises the least likely of any of the "genetic" approaches being developed for elimination of invasive fish to face serious public concern and opposition (Thresher et al. 2014). Further, the efficacy of the "daughterless" approach initially disclosed by Thresher et al. has been called into question, at least as to common carp (Zhang 2016).

References cited in and/or relevant to this "Summary" section:

Cotton, S., and C. Wedekind, 2007. Control of introduced species using Trojan sex chromosomes. Trends in Ecology and Evolution 22:441-443.

Liu, H., R. Guan, J. Xu, C. Hon, H. Tian, and H. Chen, 2013. Genetic manipulation of sex ration for the large-scale breeding of YY super-male and XY all-male Yellow Catfish (*Pelteobagrus fulvidraco* (Richardson)). Marine Biotechnology 15:321-328).

Mair, G. C., J. S. Abucay, D. O. F. Skihinski, T. A. Abella, and J. A. Beardmore, 1997, Genetic manipulation of sex ratio for the large-scale production of all-male tilapia *Oreochromis niloticus*. Canadian Journal of Fisheries and Aquatic Sciences, 54:396-404.

Muir, W. M., and R. D. Howard, 2004. Characterization of environmental risk of genetically engineered (GE) organisms and their potential to control exotic invasive species. Aquatic Sciences 66:414-420.

Schill D. J., J. A. Heindel, M. R. Campbell, K. A. Meyer, and E. R. J. M. Mamer, 2016. Production of a YY Male Brook Trout broodstock for potential eradication of undesired Brook Trout populations. North American Journal of Aquaculture 78:72-83.

Senior, A. M, P. M. Lokman, G. P. Closs, and S. Nakagawa, 2015. Ecological and evolutionary applications for environmental sex reversal of fish. The Quarterly Review of Biology 90:23-44.

Thresher, R, Grewe, P., Patil, J. and L. Hinds, 2004. Genetic control of sex ratio in animal populations. United States Patent Application Publication 2004/0073959 A1.

Thresher, R. E., K. Hayes, N. J. Bax, J. Teem, T. J. Benfey, and F. Gould, 2014. Genetic control of invasive fish: technological options and its role in integrated pest management. Biological Invasions 16:1201-1216.

According to a first exemplary embodiment, therefore, this disclosure describes a method of creating a YY animal broodstock, wherein the broodstock includes only sperm-producing YY males and egg-producing YY males, the method comprising the steps of: (a) creating YY males via androgenesis; (b) exposing selected ones of the YY males created in step (a) to a feminizing hormone; and (c) identifying sperm-producing YY males and egg-producing YY males from among the YY males created in steps (a) and (b).

In another exemplary embodiment, the method may further comprise the steps of: (d) repeating steps (a) through (c) N times in order to produce N unrelated families of sperm-producing YY males and egg-producing YY males; and (e) cross-breeding various ones of the unrelated families produced in step (d) in order to produce a genetically-diverse YY progeny. In some embodiments, N may be about 60.

In another exemplary embodiment, the method may further comprise the step of: (f) following step (e), exposing the genetically-diverse YY progeny to a feminizing hormone.

In some embodiments, about 50% of the YY males created in step (a) may be exposed to a feminizing hormone in step (b). In some embodiments, step (c) may be enabled by genetic sex marker screening. In some embodiments, step (b) may further include batch marking of the YY males exposed to a feminizing hormone in step (a). Preferably, the batch marking may be by use of a recessive hereditary color morph.

This disclosure further describes YY fish broodstocks created according to disclosed method embodiments. In other embodiments, YY broodstocks created according to disclosed method embodiments may be of other animals, including shellfish, frogs or toads, The foregoing has rather broadly outlined some features and technical advantages of the disclosed YY male broodstock development technology, in order that the following detailed description may be better understood. Additional features and advantages of the disclosed technology may be described. It should be appreciated by those skilled in the art that the conception and the specific embodiments disclosed may be readily utilized as a basis for modifying or designing other structures for carrying out the same inventive purposes of the disclosed technology, and that these equivalent constructions do not depart from the spirit and scope of the technology as described and claimed.

BRIEF DESCRIPTION OF THE DRAWINGS

For a more complete understanding of the embodiments described in this disclosure, and their advantages, reference is made to the following detailed description taken in conjunction with the accompanying drawings, in which.

DETAILED DESCRIPTION

Figure 1:
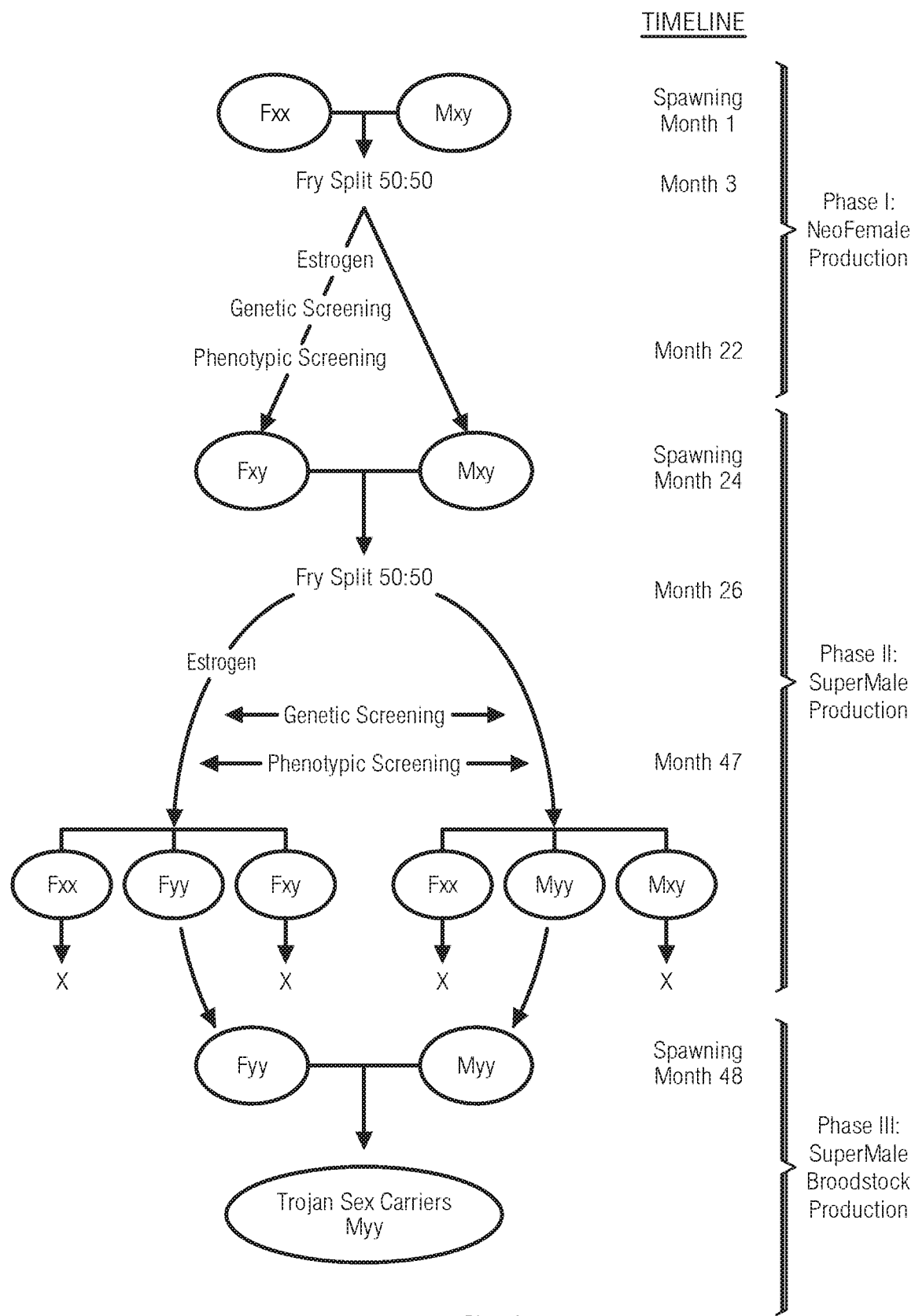
FIG. 1 is a depiction of the prior art 3-generation development of a YY male fish broodstock.

FIG. 1 illustrates the prior art for comparison purposes (e.g. Schill et al., 2016). FIG. 1 depicts a prior art method of developing a YY male fish broodstock in 3 generations. For illustrative purposes, FIG. 1 also depicts a timeline alongside the depicted prior art methodology, and shows that FIG. 1's prior art time to identify a YY male broodstock capable of spawning with the illustrated fish species is about 4 years. With momentary reference now to FIG. 3A, the comparable timeline to identify a corresponding YY male broodstock according to the disclosed YY male broodstock development technology would advantageously be about 1 year.

Figure 2:
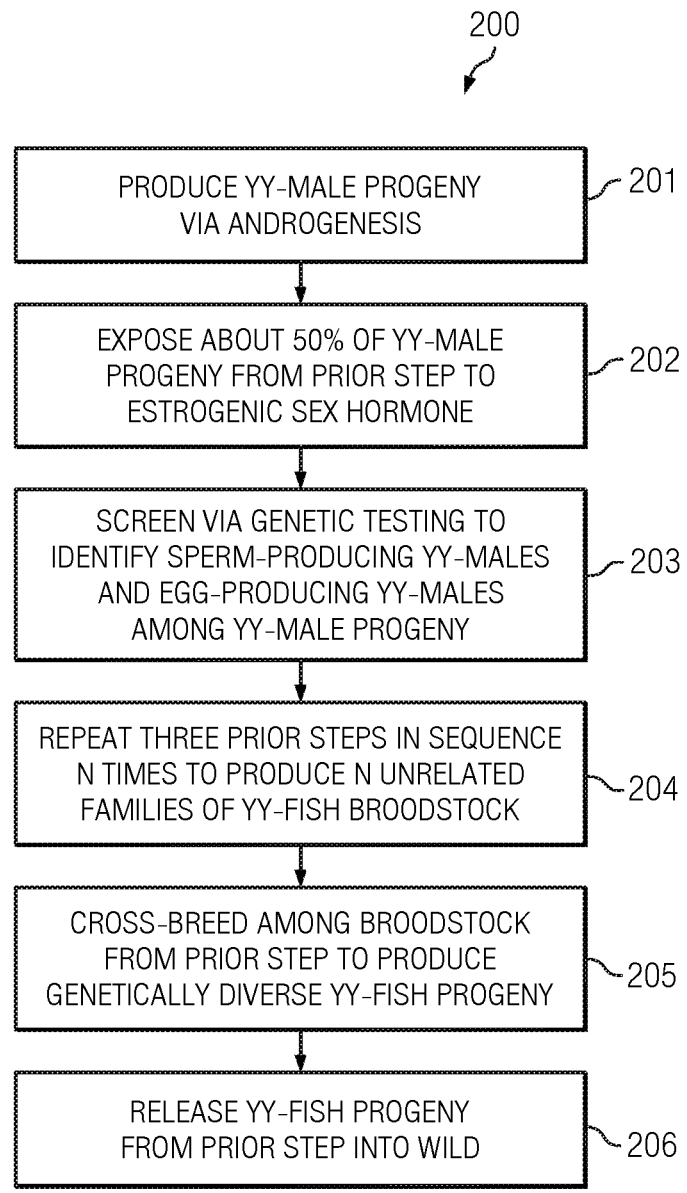
FIG. 2 is a flow chart depicting schematically, in flow chart form, one embodiment of the disclosed method of developing a YY male fish broodstock as described in more detail herein.

FIG. 2 is a flow chart depicting schematically, in flow chart form, one embodiment of the disclosed method of developing a YY male fish broodstock in a single generation as described herein, and then genetically diversifying the broodstock ready for release into the wild.

Referring to FIG. 2 in more detail, the illustrated embodiment of the disclosed method 200 comprises the following general steps. The steps are:

(1) the use of androgenesis for production of YY male progeny (block 201);

(2) timely juvenile exposure of about 50% of the YY male progeny to a selected one of several conventional estrogenic sex hormones (block 202);

(3) screening via genetic testing to identify sperm-producing YY male and egg-producing yet genetically YY male fish ("sex-reversed fish") in the broodstock (block 203) (blocks 201 to 203 preferably accomplished in a single generation);

(4) repeating steps (1) through (3) N times, to produce N unrelated families of YY fish broodstock (block 204); and (5) cross-breeding various individuals from the unrelated families created in step (4) to produce genetically diverse YY fish progeny for release into the wild (blocks 205 and 206).

It should be noted that steps (1) through (3) are capable of producing the YY male fish broodstock in one generation according to the inventive material described in this disclosure, and steps (4) and (5) are standard and conventional for cross-breeding in order to produce genetically diverse YY progeny for release into the wild.

Figure 3A:
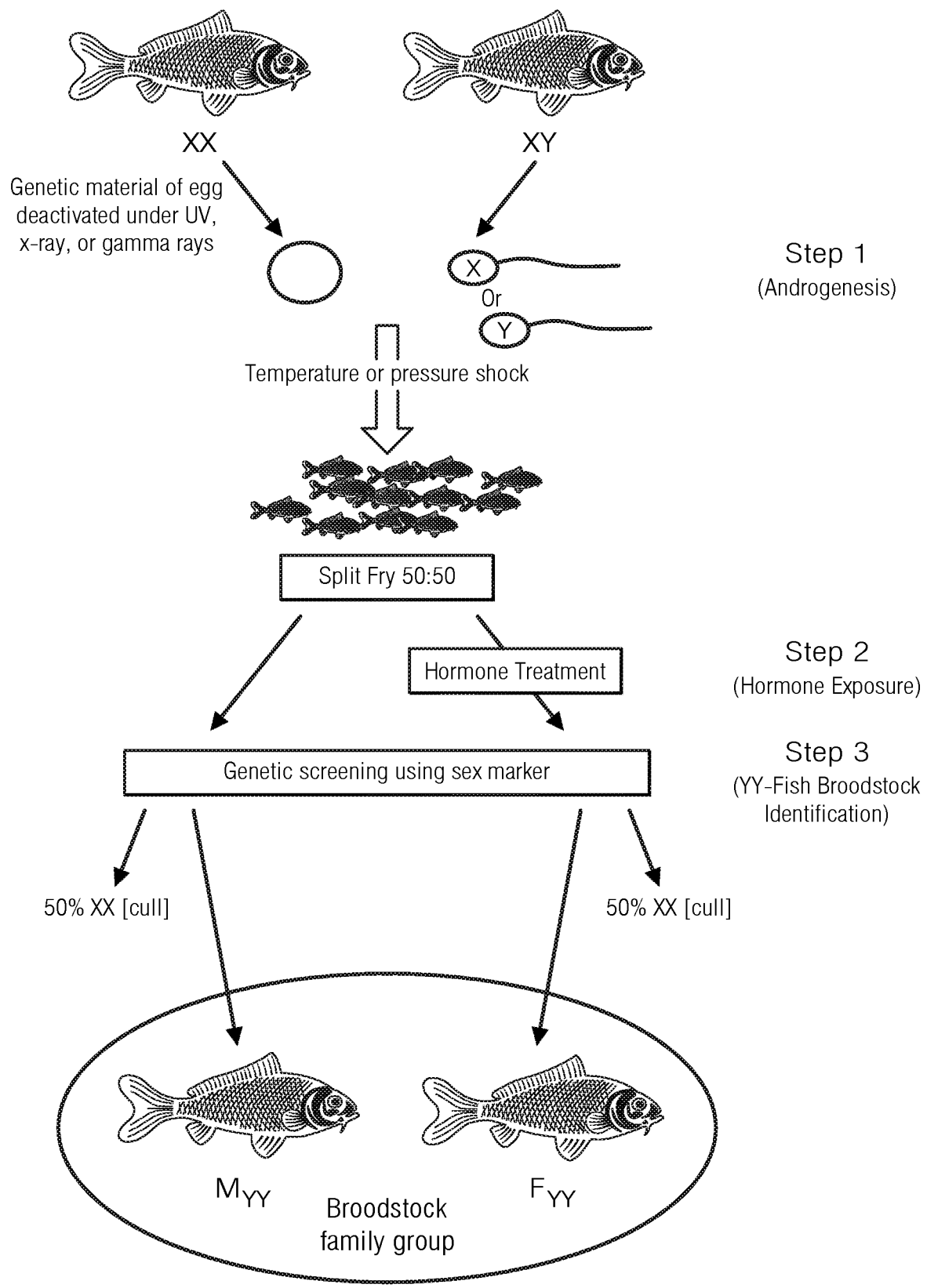
FIGS. 3A and 3B illustrate the first and second phases respectively of the exemplary embodiment of FIG. 2.
Figure 3B:
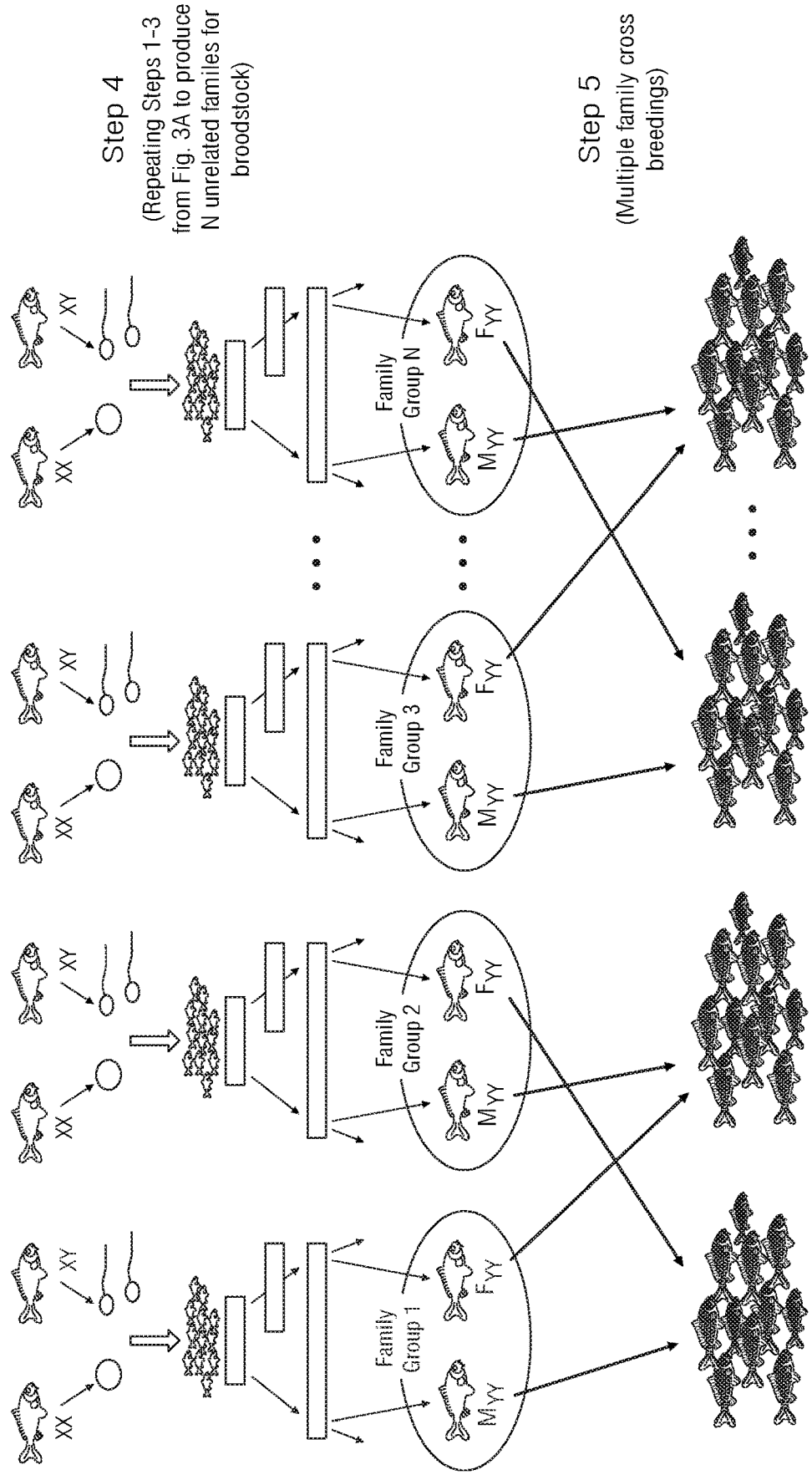

FIGS. 3A and 3B together illustrate in more detail the embodiment of the new method to develop a YY male fish broodstock according to FIG. 2. Referring first to FIG. 3A, step 1 in the disclosed process utilizes androgenesis, a known process used to produce viable fish devoid of maternal DNA. The process requires the complete deactivation of all DNA in the egg prior to fertilization by exposure to an external energy source which can take the form of UV light, X-ray radiation, or gamma radiation, depending on the size of a given species egg. Subsequent fertilization of this egg results in a haploid organism (1n) typically with a very short lifespan. However, if either a temperature or pressure shock is applied to the egg at the time of first mitotic division, the resulting organism becomes a viable 2n organism that has inherited only paternal origin DNA. Examples of conventional equipment that may be used in this androgenesis step include a Sound-Eklin portable X-Ray machine or Spectroline XX_15G short wave UV light, a Thermo M79735 scientific rocking shaker table, a hydraulic pressure chamber, model HPC™, built by TRC Hydraulics Inc., Dieppe, New Brunswick, Canada, and a VWR 1104 scientific heat bath.

With continuing reference to FIG. 3A, step 2 in the disclosed process feminizes selected ones (preferably about 50%) of the YY male fish produced in step 1, preferably via exposure to one of several available estrogenic substances including both natural hormones (Estradiol or Estrone) or synthetic ones (EE; Ethinylestradiol). In all invasive species of interest this step requires exposure of individual eggs, alevins, fry, or fingerlings to a female hormone prior to and during a defined period of sexual differentiation during which phenotype can often be altered. In most cases, estrogens are applied to the fish either by top-coating food or by immersing them in water containing known concentrations of the hormone for a specific interval in their development (e.g. Schill et al. 2016). In some slower differentiating species like the Asian carps, the hormone may need to be metered out over longer periods in very small doses via use of silastic implants (Shelton and Mims 2003). As noted, in the embodiments illustrated on FIG. 3A, preferably about half the androgenic eggs or progeny of the family would be exposed to hormones while the remaining portion would not. If the exposure timing and magnitude of estrogenic exposures of the treated group are both done correctly, hormone-treated YY male fish created in step one above will become sex-reversed, i.e. egg producers, while those progeny not exposed to hormones would remain sperm producers. It will also be understood that the disclosed technology is not limited to selection of about 50% of the androgenic eggs to be exposed to hormones. Other embodiments may expose more or less than about 50% of the androgenic eggs to hormones.

With continuing reference to FIG. 3A, step 3 in the disclosed process identifies YY males in the broodstock (whether feminized FYY or sperm-producing MYY fish) from standard XX females. With further reference to FIG. 3A, as fish in each family mature it becomes impractical (if not impossible) to determine phenotypically which of the egg-producing fish in the treated groups are hormone-treated YY male fish, and which are standard XX female fish. Numerically, on average, about half the fish in each "family" would actually be standard XX females. As illustrated on FIG. 3A, step 3 uses genetic sex markers (e.g. Schill et al, 2016) as a screening tool to identify which of the individuals are standard XX females and, in the hormone treated group, which are actually feminized YY males. The genetically identified XX females in either group are non-essential and are culled. The combined remainders from each group comprise a YY broodstock created in a single generation. Upon full maturation within the broodstock, the feminized YY males can then be bred to the androgenic sperm-producing YY males (that were not exposed to estrogenic substances) to create large numbers of progeny for subsequent release as TYC agents. In currently preferred embodiments, the sex identification in step 3 is accomplished using a nucleotide sequencer. The Illumina Next Gen sequencer is an example of a recently-available brand of equipment capable of efficiently testing for sex via restriction-site associated DNA sequencing (RAD-seq) technology and single nucleotide polymorphisms or SNPs.

As noted, steps 1 through 3 on FIG. 3A are preferably accomplished in a single generation. With reference now to FIG. 3B, step 4 in the disclosed process is to repeat steps 1 through 3 (as depicted in FIG. 3A) N times, where in currently preferred embodiments, N is about 60 times. Note, however, that this disclosure is not limited to any specific value for N. At the completion of step 4, N unrelated families of YY fish (where N is currently preferred to be about 60) comprising the YY broodstock will then be available for cross-breeding in step 5.

FIG. 3B illustrates such cross-breeding (step 5), resulting in genetically diverse YY progeny for release into the wild. A sub-sample of individuals from each family would be cross-spawned with other unrelated family progeny of the opposite sex to maximize genetic diversity. As a result, large numbers of genetically-diverse broodstock progeny (all sperm-producing YY males) thus become available for release into wild populations, and all their eventual progeny (the result of breeding with wild XX females) will be 100% XY (or regular) males (Parshad 2011, Schill et al. 2016). Continued stocking of the YY males developed by the disclosed new process will eventually create an all-male wild population, thereby starving the wild population of its ability to produce eggs and further reproduce. The end result is substantial, if not complete eradication of the undesired invasive species in a given waterway.

Figure 4:
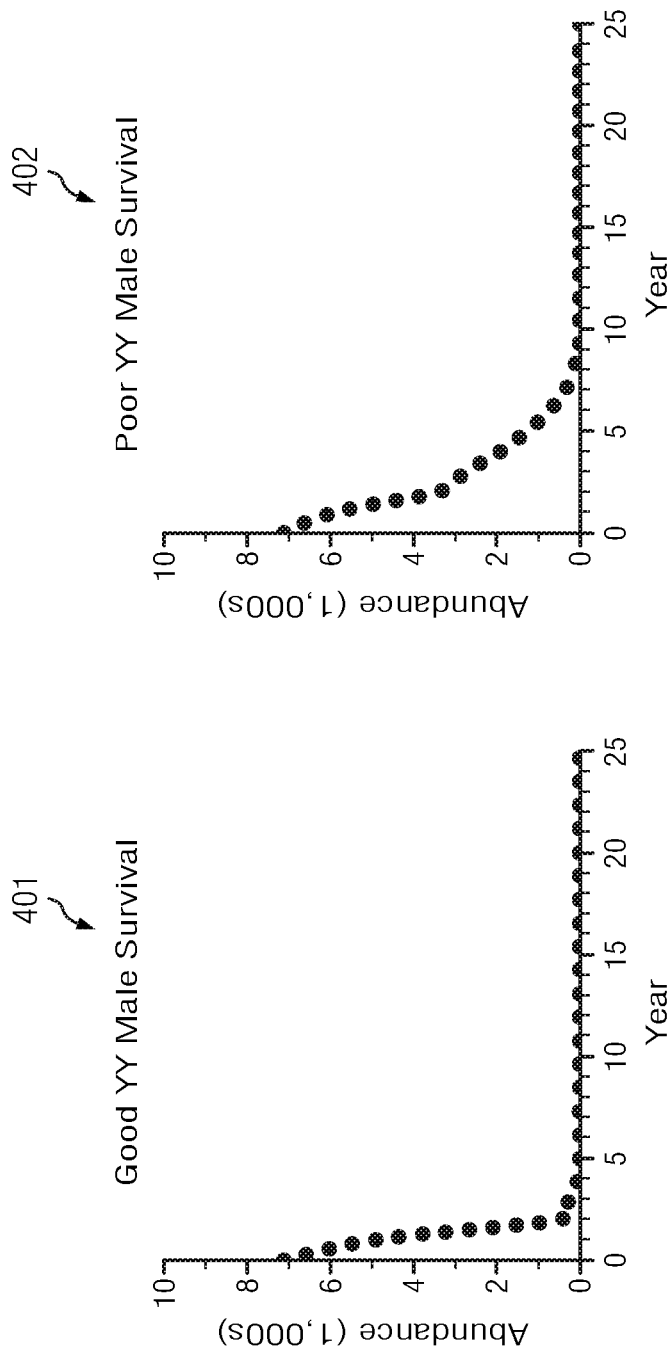
FIG. 4 illustrates graphically an example of the predicted effects of stocking sperm-producing YY male Brook Trout when used in conjunction with manual removal and considering two levels of stocked YY male survival in the wild.

FIG. 4 illustrates graphically an example of the predicted effects of stocking sperm-producing YY male Brook Trout when used in a stream population in conjunction with manual removal (Schill et al. 2017). As illustrated on FIG. 4, the predicted time to complete eradication ranges from about 4 years to about 10 years, time frames certainly of interest to fisheries managers. In FIG. 4, each graph is a simulated abundance of trout in a hypothetical 10-km Idaho stream subjected to a range of electro-fishing removals and stocking of YY male Brook Trout. Good YY male survival is depicted on graph 401 on FIG. 4, when YY males survive and reproduce at about the same rate as normal wild males. Poor YY survival is depicted on graph 402 on FIG. 4, when YY males survive and reproduce at about one-fifth of the rate of normal wild males. Graphs 401 and 402 both assume 50% manual removal (suppression) and 50% YY male stocking.

Variations

The scope of this disclosure is not limited to fish species. One possible variation of the approach may relate to other entire classes of invasive animals. Two species of Dreissenid mussels (Quagga and Zebra mussels) currently comprise two of the most destructive and fastest spreading invasives in the Mississippi River basin (United States). In addition, they have spread to several western USA waters, the most notable being Lake Mead in Arizona, and are currently a formidable ecosystem threat in lentic and lotic waters nationwide. Although to date, discussion of the use of YY Males in a TYC program has been limited to invasive fish, numerous shellfish species are sensitive to estrogenic substances (Andrew et al. 2010; Gagne et al. 2003) and many can be raised in captivity. Thus, destructive invasive shellfish species such as Quagga and Zebra mussels may be combatted using the TYC approach if rapid development of a broodstock proved feasible. A similar possibility exists for invasive frogs and toads including the cane toad in Australia, a species which initially drove interest in the development of the daughterless transgenic construct.

Another potential variation within the scope of this disclosure is that the androgenesis portion of the approach (Step 1 on FIG. 3A) may enable batch "marking" of all YY males to be released into the wild. Preferably, the batch marking may be by recessive hereditary color morph during androgenesis, although this disclosure is not limited in this regard. An external appearance or condition (mark) of YY individuals would allow for a much more effective selective removal program where wild fish of both sexes would be manually removed and the "marked" YY males returned to study waters unharmed. Such a selective removal approach has been demonstrated in simulation studies to result in much more rapid eradication of invasive fish than when a non-selective removal method is used (Thresher et al. 2013; Schill et al. 2017). Marking would be possible in those species with readily visible homozygous recessive traits such as the mirror carp variants in common carp populations. While such visible homozygous traits are sometimes used to ensure that all maternal genetic influence has been successfully deactivated in the androgenesis process, the same phenotypic characteristic (if not selected against in the wild, e.g. possibly mirror carp) could be used to identify all future stocked YY males in the wild and thus improve their efficacy for use in a TYC eradication program.

A further variation within the scope of this disclosure is the implementation of an additional step. In other work involving the release of YY male fish into the environment, (Kennedy et al. in press), the authors relied on the release of sperm-producing YY fish ($M_{YY}$ fish) as first suggested in a theoretical simulation paper (Parshad 2011). However, the initial inspiration and theoretical modeling of the TYC concept relied on the largescale release of feminized YY males ($F_{YY}$ fish) into the wild (Gutierrez and Teem 2006). The latter approach may be more efficient in eradicating species because half of the progeny from the union of a stocked $F_{YY}$ fish and a wild XY male would also be YY, a result that may speed the eradication process (Gutierrez and Teem 2006; Teem and Gutierrez 2010). In the United States, the release of a feminized food-producing fish involves increased oversight by the U.S. Food and Drug administration (even though examples of this practice exist). However, to date no known simulation studies have been done directly comparing the relative merit and eradication efficiency of the $M_{YY}$ versus $F_{YY}$ release approach. If the latter approach appears necessary for the successful eradication of some invasive species, then a final step (feminization of all $M_{YY}$ broodstock progeny before release) would become a useful variant within the scope of this disclosure.

References cited in and/or relevant to this Detailed Description section:

Andrew, M. N., O'Conner, W. A., Dunstan, R. H., and G. R. MacFarlane, 2010 Exposure to 17 alpha ethynylestradiol causes dose and temporally dependent changes intersex, females and vitellogenin production in the Sydney rock oyster. Ecotoxicology 19: 1440-1451.

Gagne, F., Blaise, C., Pellerin, J., Pelletier, E., Douville, M., Gauthier-Clerc, S., and L Viglino 2003. Sex alteration in soft-shell clams in an intertidal zone of the Saint Lawrence River, Quebec, Canada. Comparative Biochemistry and Physiology Part C 134: 189-198.

Gutierrez, J. B., and J. L. Teem, 2006. A model describing the effect of sex-reversed YY fish in an established wild population: the use of a Trojan Y chromosome to cause extinction of an introduced exotic species. Journal of Theoretical Biology 241:333-341.

Kennedy, P., K. A. Meyer, D. J. Schill, M. R. Campbell, N. Vu, and N. V. Vu. in press. Survival and reproductive success of hatchery YY male Brook Trout stocked in Idaho Streams. North American Journal of Fisheries Management.

Kogan, M., 1998. Integrated pest management: Historical perspectives and contemporary developments. Annual Review of Entomology 43:243-70.

Parshad, R. D., 2011. Long time behavior of a PDE model for invasive species control. International Journal of Mathematical Analysis 5:1991-2015.

Schill D. J., J. A. Heindel, M. R. Campbell, K. A. Meyer, and E. R. J. M. Mamers, 2016. Production of a YY Male Brook Trout broodstock for potential eradication of undesired Brook Trout populations. North American Journal of Aquaculture 78:72-83.

Schill, D. J., K. A. Meyer, and M. J. Hansen, 2017 Simulated effects of YY Male stocking and manual suppression for eradicating non-native Brook Trout populations. North American Journal of Fisheries Management 37:5, 1054-1066.

Shelton, W. L. and S. D. Mims, 2003. Fabrication of Silastic Implants for in Vivo Steroid Delivery in Fish, North American Journal of Aquaculture, 65:2, 158-161.

Them, J. L., and J. B. Gutierrez, 2010. A theoretical strategy for eradication of Asian Carps using a Trojan Y Chromosome to shift the sex ratio of the population. American Fisheries Society Symposium 74:1-12.

Thresher, R. E., K. Hayes, N. J. Bax, J. Teem, T. J. Berfey, and F. Gould 2013. Genetic control of invasive fish: technological options and its role in integrated pest management. Biological Invasions 16:1201-1216.

Although the inventive material in this disclosure has been described in detail along with some of its technical advantages, it will be understood that various changes, substitutions and alternations may be made to the detailed embodiments without departing from the broader spirit and scope of such inventive material as set forth in the following claims.

I claim:

1. A method of creating a YY animal broodstock, wherein the broodstock includes only sperm-producing YY males and egg-producing YY males, the method comprising:
   (a) using androgenesis to create a first generation of juvenile XX females and juvenile YY males;
   (b) exposing a predetermined portion of the first generation created in step (a) to a feminizing hormone while the first generation created in step (a) are still juveniles, such that following step (b), a post-exposure first generation includes juvenile XX females and juvenile YY males in which at least some of the juvenile XX females and at least some of the juvenile YY males therein have been exposed to the feminizing hormone; and
   (c) following step (b), screening the post-exposure first generation for, and separating out, future sperm-producing YY males and future egg-producing YY males, thereby creating a YY animal broodstock.

2. The method of claim 1, in which step (c) is enabled by genetic sex marker screening.

3. The method of claim 1, in which step (c) is performed while the first generation are still juveniles.

4. The method of claim 1, in which the predetermined portion in step (b) is about 500/0.

5. The method of claim 1, further comprising the steps of:
   (d) repeating steps (a) through (c) N times to produce N unrelated families of sperm-producing YY males and egg-producing YY males; and
   (e) cross-breeding various ones of the unrelated families produced in step (d) in order to produce a genetically-diverse YY progeny.

6. The method of claim 5, in which N is about 60.

7. The method of claim 5, further comprising the step of:
   (f) following step (e), and while the genetically-diverse YY progeny are still juveniles, exposing the genetically diverse YY progeny to a feminizing hormone.

8. The method of claim 1, in which step (a) further includes batch marking of the YY males during androgenesis.

9. The method of claim 8, in which the batch marking is by use of a recessive hereditary color morph.

10. A YY animal broodstock created according to the method of claim 1, in which the YY animal broodstock is selected from the group consisting of (1) fish; (2) shellfish; (3) frogs and (4) toads.

11. A method of creating a YY animal broodstock, wherein the broodstock includes only sperm-producing YY males and egg-producing YY males, the method comprising:
   (a) using androgenesis to create a first generation of juvenile XX females and juvenile YY males;
   (b) exposing a predetermined portion of the first generation created in step (a) to a feminizing hormone while the first generation created in step (a) are still juveniles, such that following step (b), a post-exposure first generation includes juvenile XX females and juvenile YY males in which at least some of the juvenile XX females and at least some of the juvenile YY males therein have been exposed to the feminizing hormone; and
   (c) following step (b), using genetic sex marker testing to screen the post-exposure first generation for, and separate out, future sperm-producing YY males and future egg-producing YY males, thereby creating a YY animal broodstock.

12. The method of claim 11, in which step (c) is performed while the first generation are still juveniles.

13. The method of claim 11, in which the predetermined portion in step (b) is about 50%.

14. The method of claim 11, further comprising the steps of:
   (d) repeating steps (a) through (c) N times to produce N unrelated families of sperm-producing YY males and egg-producing YY males; and
   (e) cross-breeding various ones of the unrelated families produced in step (d) in order to produce a genetically-diverse YY progeny.

15. The method of claim 14, further comprising the step of:
   (f) following step (e), and while the genetically-diverse YY progeny are still juveniles, exposing the genetically diverse YY progeny to a feminizing hormone.

16. The method of claim 11, in which step (a) further includes batch marking of the YY males during androgenesis.

17. The method of claim 16, in which the batch marking is by use of a recessive hereditary color morph.

18. A method of creating a YY animal broodstock, wherein the broodstock includes only sperm-producing YY males and egg-producing YY males, the method comprising:
   (a) using androgenesis to create a first generation of juvenile XX females and juvenile YY males;
   (b) exposing a predetermined portion of the first generation created in step (a) to a feminizing hormone while the first generation created in step (a) are still juveniles, such that following step (b), a post-exposure first generation includes juvenile XX females and juvenile YY males in which at least some of the juvenile XX females and at least some of the juvenile YY males therein have been exposed to the feminizing hormone; and
   (c) following step (b), and while the first generation are still juveniles, using genetic sex marker testing to screen the post-exposure first generation for, and separate out, future sperm-producing YY males and future egg-producing YY males, thereby creating a YY animal broodstock.

19. The method of claim 18, in which the predetermined portion in step (b) is about 500/0.

20. The method of claim 18, further comprising the steps of:
   (d) repeating steps (a) through (c) N times to produce N unrelated families of sperm-producing YY males and egg-producing YY males;
   (e) cross-breeding various ones of the unrelated families produced in step (d) in order to produce a genetically-diverse YY progeny; and
   (f) following step (e), and while the genetically-diverse YY progeny are still juveniles, exposing the genetically diverse YY progeny to a feminizing hormone.

\* \* \* \* \*

UNITED STATES PATENT AND TRADEMARK OFFICE
CERTIFICATE OF CORRECTION

PATENT NO. : 10,638,733 B2
APPLICATION NO. : 16/536022
DATED : May 5, 2020
INVENTOR(S) : Daniel J. Schill Page 1 of 1

It is certified that error appears in the above-identified patent and that said Letters Patent is hereby corrected as shown below:

In the Specification

Column 3, Line 15, "Bowers" should read --Bongers--.

Column 3, Line 24, "Xiang" should read --Jiang--.

Column 3, Line 29, "Them" should read --Teem--.

Column 3, Line 53, "Groyne" should read --Grewe--.

Column 3, Line 58, "44-454" should read --445-454--.

Column 5, Line 13, "Hon" should read --Hou--.

Column 5, Line 18, "Skihinski" should read --Skibinski--.

Column 10, Line 41, "Mamers" should read --Mamer--.

Column 10, Line 53, "Them" should read --Teem--.

Column 10, Line 57, "Berfey" should read --Benfey--.

In the Claims

Claim 4 at Column 11, Line 26, "500/0" should read --50%--.

Claim 19 at Column 12, Line 48, "500/0" should read --50%--.

Signed and Sealed this
Thirteenth Day of April, 2021

Drew Hirshfeld
*Performing the Functions and Duties of the
Under Secretary of Commerce for Intellectual Property and
Director of the United States Patent and Trademark Office*